US009446156B2

(12) United States Patent
Gorgerat et al.

(10) Patent No.: US 9,446,156 B2
(45) Date of Patent: Sep. 20, 2016

(54) GAS-FILLED MICROVESICLES WITH POLYMER-MODIFIED LIPIDS

(75) Inventors: Stephane Gorgerat, Plan-les-Ouates (CH); Christian Guillot, Plan-les-Ouates (CH); Feng Yan, Plan-les-Ouates (CH)

(73) Assignee: BRACCO SUISSE S.A., Manno (CH)

( * ) Notice: Subject to any disclaimer, the term of this patent is extended or adjusted under 35 U.S.C. 154(b) by 680 days.

(21) Appl. No.: 12/440,009

(22) PCT Filed: Sep. 4, 2007

(86) PCT No.: PCT/EP2007/059256
§ 371 (c)(1),
(2), (4) Date: Mar. 4, 2009

(87) PCT Pub. No.: WO2008/028917
PCT Pub. Date: Mar. 13, 2008

(65) Prior Publication Data
US 2009/0263330 A1    Oct. 22, 2009

(30) Foreign Application Priority Data
Sep. 5, 2006 (EP) .................................. 06120109

(51) Int. Cl.
*A61K 49/22* (2006.01)
*A61K 49/18* (2006.01)
*A61K 51/12* (2006.01)

(52) U.S. Cl.
CPC ......... *A61K 49/223* (2013.01); *A61K 49/1818* (2013.01); *A61K 51/1251* (2013.01)

(58) Field of Classification Search
CPC .................. A61K 49/1818; A61K 51/1251; A61K 49/223
USPC ....................................... 424/9.5, 9.51, 9.52
See application file for complete search history.

(56) References Cited

U.S. PATENT DOCUMENTS

| | | | |
|---|---|---|---|
| 5,271,928 A | 12/1993 | Schneider et al. | |
| 5,413,774 A | 5/1995 | Schneider et al. | |
| 5,445,813 A | 8/1995 | Schneider et al. | |
| 5,545,395 A | 8/1996 | Tournier et al. | |
| 5,556,610 A | 9/1996 | Yan et al. | |
| 5,597,549 A | 1/1997 | Schneider et al. | |
| 5,605,673 A | 2/1997 | Schutt et al. | |
| 5,733,572 A * | 3/1998 | Unger ............. | A61K 8/14 424/1.21 |
| 5,827,504 A | 10/1998 | Yan et al. | |
| 6,139,819 A | 10/2000 | Unger et al. | |
| 6,258,378 B1 | 7/2001 | Schneider et al. | |
| 6,416,740 B1 | 7/2002 | Unger | |
| 2003/0003055 A1 | 1/2003 | Unger et al. | |
| 2004/0013720 A1* | 1/2004 | Ellens ............... | A61K 9/127 424/450 |
| 2004/0141922 A1* | 7/2004 | Klaveness et al. ....... | 424/9.52 |
| 2005/0025710 A1* | 2/2005 | Schneider ........... | A61K 49/225 424/9.52 |
| 2009/0110643 A1 | 4/2009 | Maruyama et al. | |

FOREIGN PATENT DOCUMENTS

| | | |
|---|---|---|
| EP | 0554213 B2 | 8/1993 |
| EP | 0804251 B1 | 11/1997 |
| JP | 2006-063052 A | 3/2006 |
| WO | 9115244 A2 | 10/1991 |
| WO | 9409829 A1 | 5/1994 |
| WO | 9729782 A1 | 8/1997 |
| WO | 9729783 A1 | 8/1997 |
| WO | 9818501 A2 | 5/1998 |
| WO | 9955383 A2 | 11/1999 |
| WO | 02055544 A2 | 7/2002 |
| WO | 03074005 A2 | 9/2003 |
| WO | 03084574 A1 | 10/2003 |
| WO | 2004069284 A2 | 8/2004 |
| WO | 2005063305 A1 | 7/2005 |
| WO | 2005063306 A1 | 7/2005 |
| WO | 2006-126244 A1 | 11/2006 |

OTHER PUBLICATIONS

Office Action for Australian application No. 2007293888, mail date May 15, 2012.
Office Action for Canadian application No. 2,662,087, mail date Nov. 21, 2013.
Office Action for Chinese application No. 200780039088.6, mail date Dec. 27, 2010 (English translation).
Office Action for Japanese application No. 2009-527133, mail date Aug. 14, 2012 (English translation with Office Action Summary).
Office Action for Japanese application No. 2009-527133, mail date Jul. 2, 2013 (English translation with Office Action Summary).

\* cited by examiner

*Primary Examiner* — Michael G Hartley
*Assistant Examiner* — Leah Schlientz
(74) *Attorney, Agent, or Firm* — Vivicar Law, PLLC

(57) ABSTRACT

Image enhancing contrast agents for use in diagnostic and/or therapeutic methods, particularly in the form of gas-filled microvesicles, with enhanced stability. The gas-filled microvesicles are stabilized by a layer of amphiphilic material and comprise from 0.15% to 1.0% by moles of a lipid bearing a hydrophilic polymer. The lipid bearing a hydrophilic polymer is preferably a phospholipid linked to polyethyleneglycol.

14 Claims, No Drawings

GAS-FILLED MICROVESICLES WITH POLYMER-MODIFIED LIPIDS

TECHNICAL FIELD

The present invention relates to image enhancing contrast agents for use in diagnostic and/or therapeutic methods, particularly in the form of gas-filled microvesicles.

BACKGROUND OF THE INVENTION

Injectable formulations useful as contrast agents, particularly for ultrasound imaging, include suspensions of gas bubbles having a diameter of a few microns dispersed in an aqueous medium. Of particular interest are gas bubbles which are stabilized by means of suitable additives such as, for example emulsifiers, oils, thickeners or sugars, or by entrapping or encapsulating the gas or a precursor thereof in a variety of systems. These stabilized gas bubbles are generally referred to in the art as gas-filled microvesicles.

Useful gas-filled microvesicles include aqueous suspensions in which the bubbles of gas are bounded at the gas/liquid interface by a very thin envelope (film) involving a stabilizing amphiphilic material disposed at the gas to liquid interface. These suspensions are typically prepared by contacting powdered amphiphilic materials, e.g. freeze-dried preformed liposomes or freeze-dried or spray-dried lipid solutions, with air or other gas and then with an aqueous carrier, while agitating to generate a suspension of gas-filled microvesicles which can then be administered, preferably shortly after its preparation. Examples of aqueous suspension of gas-filled microvesicles and preparation thereof are disclosed, for instance, in U.S. Pat. No. 5,271,928, U.S. Pat. No. 5,445,813, U.S. Pat. No. 5,413,774, U.S. Pat. Nos. 5,556,610, 5,597,549, U.S. Pat. No. 5,827,504, WO 97/29783 and WO2004/069284, which are herein incorporated by reference in their entirety.

Among the component of lipid stabilized gas-filled microvesicles, it has also been suggested to introduce stabilizing compounds in the form of lipids bearing a hydrophilic polymer, such as phospholipids linked to a polyethyleneglycol, in variable amounts. For instance, U.S. Pat. No. 6,416,740 discloses compositions where the amount of said polymer-bearing lipid is greater than about 1 mole percent, it being at least of five mole percent when the lipid is a phospholipid bearing a polyethyleneglycol.

The Applicant has now observed that such amounts of lipids bearing a hydrophilic polymer are however not necessary to obtain stable microvesicles, as such stability can unexpectedly be obtained at very low concentrations of lipids bearing a hydrophilic polymer. The Applicant has further observed that such low amounts of lipids bearing a hydrophilic polymer may allow to entrap higher volumes of gas into the microvesicles. In addition, the Applicant has also observed that such very low concentrations of lipids bearing a hydrophilic polymer may also surprisingly result in an increased number of microvesicles.

SUMMARY OF THE INVENTION

An aspect of the invention relates to gas-filled microvesicles stabilized by a layer of amphiphilic material comprising from 0.15% to 1.0% by moles of a lipid bearing a hydrophilic polymer. Preferably said concentration is of at least 0.3% by moles and more preferably of about 0.5% by moles.

The lipid bearing the hydrophilic polymer is preferably a phospholipid covalently linked to a polyethylenglycol.

Further aspects of the invention include respective precursors of said microvesicles, particularly in the form of a dry powder comprising said amphiphilic material and said lipid bearing a hydrophilic polymer, pharmaceutical kits comprising said microvesicles or a precursor thereof, methods of manufacturing said microvesicles and methods of using said microvesicles.

DETAILED DESCRIPTION OF THE INVENTION

Gas-filled microvesicles as defined herein comprise dispersions of gas bubbles of micronic and sub-micronic size in an aqueous suspension comprising an amphiphilic compound. At least a portion of the amphiphilic compound is disposed at the gas to liquid interface, thus forming a thin envelope (typically in the form of a film) conferring the desired stability to the gas bubbles.

Amphiphilic compounds useful for forming the stabilizing envelope can be synthetic or naturally-occurring biocompatible compounds and may include, for example a film forming lipid, in particular a phospholipid. Examples of amphiphilic compounds include, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol isobutyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy) hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

Depending on the combination of components and on the manufacturing process of the microvesicles, the above listed exemplary compounds may be employed as main compound for forming the microvesicles envelope or as simple additives, thus being present only in minor amounts.

According to a preferred embodiment, at least one of the compounds forming the microvesicles' envelope is a phospholipid, optionally in admixture with any of the other above cited film-forming materials. According to the present description, the term phospholipid is intended to encompass any amphiphilic phospholipid compound, the molecules of which are capable of forming a stabilizing film of material at the gas-water boundary interface in the final microvesicles suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such as, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoyl-phosphatidic acid (DAPA) and its alkali metal salts, dimyristoyl-phosphatidylethanolamine (DMPE), dipalmitoylphosphatidylethanolamine (DPPE), distearoyl phosphatidylethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Particularly preferred phospholipids are DAPC, DSPC, DPPA, DSPA, DMPS, DPPS, DSPS and Ethyl-DSPC. Most preferred are DPPS or DSPC.

Mixtures of phospholipids can also be used, such as, for instance, mixtures of DPPE, DPPC, DSPC and/or DAPC with DSPS, DPPS, DSPA, DPPA, DSPG, DPPG, Ethyl-DSPC and/or Ethyl-DPPC.

In preferred embodiments, the phospholipid is the main component of the stabilizing envelope of microvesicles, amounting to at least 50% (w/w) of the total amount of components forming the envelope of the gas filled microvesicles. In some of the preferred embodiments, substantially the totality of the envelope (i.e. at least 90% and up to 100% by weight) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred is palmitic acid.

According to a preferred embodiment, the envelope of microvesicles forming a composition of the invention includes a compound bearing an overall (positive or negative) net charge. Said compound can be a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also the lyso-form of the above cited phospholipids, such as lysophosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compound. Examples of negatively charged lipids are bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salt, stearic acid salt, 1,2-dipalmitoyl-sn-3-succinylglycerol salt or 1,3-dipalmitoyl-2-succinylglycerol salt.

Preferably, the negatively charged compound is selected among DPPA, DPPS, DSPG or mixtures thereof.

The negatively charged component is typically associated with a corresponding positive counter-ion, which can be mono- (e.g. an alkali metal or ammonium), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). The negative counterion is preferably an halogen ion, in particular chlorine or bromine. Examples of positively charged lipids are alkylammonium salts with a halogen counter ion (e.g. chlorine or bromine) comprising at least one ($C_{10}$-$C_{20}$), preferably ($C_{14}$-$C_{18}$), alkyl chain, such as, for instance mono or di-stearylammonium chloride, mono or di-hexadecylammonium chloride, dimethyldioctadecylammonium bromide (DDAB), hexadecyltrimethylammonium bromide (CTAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

The positively charged component is typically associated with a corresponding negative counter-ion, which can be mono- (e.g. halogen), di- (e.g. sulphate) or tri-valent (e.g. phosphate). Preferably the counter-ion is selected among halogen ions, such as $F^-$ (fluorine), $Cl^-$ (chlorine) or $Br^-$ (bromine).

Mixtures of neutral and charged compounds, in particular of phospholipids and/or lipids, can be satisfactorily employed to form the microvesicles envelope. The amount of charged lipid or phospholipid may vary from about 95% to about 1% by mole, with respect to the total amount of lipid and phospholipid, preferably from 80% to 20% by mole.

Preferred mixtures of neutral phospholipids and charged lipids or phospholipids are, for instance, DPPG/DSPC, DPPG/DAPC, DPPS/DSPC, DPPS/DAPC, DPPE/DPPG, DSPA/DAPC, DSPA/DSPC and DSPG/DSPC.

According to the present invention, the amphiphilic material comprised in the aqueous suspension further comprises from 0.15% to 1.0% of a lipid bearing a hydrophilic polymer (hereinafter referred to as "polymer-modified lipid"). Preferably said concentration is of at least 0.3% by moles and more preferably of about 0.5% by moles. The lipid is preferably a phospholipid, more preferably a phosphatityle-thanolamine, in particular a fatty acid di-ester of phosphatidylethanolamine such as the above cited DMPE, DPPE, DSPE, DOPE, DAPE or DLPE. The hydrophilic polymer associated with the lipid is preferably covalently bound therewith. Said polymer has a molecular weight of from about 500 to about 50,000 Daltons, preferably from about 1,000 to about 20,000 daltons and even more preferably of from about 2,000 to about 10,000 daltons. Suitable hydrophilic polymers are and can be selected among chitin, hyaluronic acid, polyethyleneglycol (PEG), polypropyleneglycol (PPG), polyvinylalcohol (PVA), polyvinylpirrolidone (PVP), polyacrylamide, poly(acetyethyleneimine), polyethylenimine (PEI), polycyanoacrylate, polylactic acid (PLA), poly(lactide-co-glycolide) (PLGA) and mixtures and copolymers thereof. The polymer can advantageously be a biocompatible and/or biodegradable polymer. Preferably the hydrophilic polymer is PEG, with a molecular weight of from 1,000 to about 10,000 daltons, preferably from 4,000 to 7,500 daltons. Preferred examples of polymer-modified lipids are phosphatidylethanolamines modified with polyethylenglycol (PEG), i.e. phosphatidylethanolamines where the hydrophilic ethanolamine moiety is covalently linked to a PEG molecule of variable molecular weight. The acronym PEG identifies either polyethyleneglycols as such, as well as any modified modification thereof, including polyethyleneglycols bearing protective or reactive groups. For instance, it includes MPEG, i.e. polyethyleneglycols where the terminal hydroxyl moiety thereof is methylated. According to a preferred embodiment, a phosphatidylethanolamine, particularly DPPE or DSPE, is combined with polyethylene glycols of different molecular weight, such as, for instance PEG2000, PEG4000 or PEG5000 (i.e. polyethylene glycols of mean MW of 2000, 4000 or 5000, respectively), to form respective pegylated phospholipids (e.g. DPPE-PEG of DSPE-PEG) of corresponding molecular weight. Suitable commercial pegylated lipids are available, for instance from Genzyme (Massachusetts, USA). Other suitable polymer-modified lipids are pegylated lipids where a PEG is covalently linked through an ester bond to a fatty acid (e.g. polyoxyethyleneglycol palmitate, stearate, laurate or oleate) commercially available, for instance, under the trademark name Myrj®, or pegylated lipids where a PEG is covalently linked through an ether bond to a fatty alcohol (e.g. polyoxyethyleneglycol lauryl-, cetyl-, stearyl- or oleyl-ether) commercially available, for instance under the trademark Brij®.

As previously mentioned, the Applicant has observed that with a low amount of polymer-modified lipid it is possible to obtain gas-filled microvesicles which are at least as stable as comparative microvesicles comprising higher amounts of polymer-modified lipid. In addition, such a low amount of polymer-modified allows obtaining a relatively larger number of gas-filled microvesicles and to incorporate higher volumes of gas into the microvesicles, with respect to compositions comprising higher amounts of polymer-modified lipids.

In general, lower amounts of lipids bearing polymers with higher molecular weight may be employed with respect to corresponding lipids bearing polymers with lower molecular weight, nevertheless obtaining similar results.

In some instances, particularly when the polymer-modified lipid is a phospholipid combined with a PEG as above defined (e.g. pegylated phosphatidylethanolamine), it may be desirable to increase its relative amount up to about 5.0% by moles, preferably up to 3.0% by moles.

Other excipients or additives may be present either in the dry formulation of the microvesicles or may be added together with the aqueous carrier used for the reconstitution thereof, without necessarily being involved (or only partially involved) in the formation of the stabilizing envelope of the microvesicle. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars, hydrophilic polymers like polyethylene glycol.

As the preparation of gas-filled microvesicles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyglycol such as polyethylene glycol.

Any biocompatible gas, gas precursor or mixture thereof can be employed to prepare the microvesicles of the invention.

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or prefluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_6F_{14}$, $C_7F_{14}$, $C_7F_{16}$, $C_8F_{18}$, and $C_9F_{20}$.

Particularly preferred gases are $SF_6$ or perfluorocarbons selected from $CF_4$, $C_2F_6$, $C_3F_8$, $C_4F_8$, $C_4F_{10}$ or mixtures thereof; $SF_6$, $C_3F_8$ or $C_4F_{10}$ are particularly preferred.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, preferably selected from $SF_6$, $CF_4$, $C_2F_6$, $C_3F_6$, $C_3F_8$, $C_4F_6$, $C_4F_8$, $C_4F_{11}$, $C_5F_{10}$, $C_5F_{12}$ or mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

For ultrasonic echography, the biocompatible gas or gas mixture is preferably selected from air, nitrogen, carbon dioxide, helium, krypton, xenon, argon, methane, halogenated hydrocarbons (including fluorinated gases such as perfluorocarbons and sulfur hexafluoride) or mixtures thereof. Advantageously, perfluorocarbons (in particular $C_4F_{10}$ or $C_3F_8$) or $SF_6$ can be used, optionally in admixture with air or nitrogen.

For the use in MRI the microvesicles will preferably contain a hyperpolarized noble gas such as hyperpolarized neon, hyperpolarized helium, hyperpolarized xenon, or mixtures thereof, optionally in admixture with air, $CO_2$, oxygen, nitrogen, helium, xenon, or any of the halogenated hydrocarbons as defined above.

For use in scintigraphy, the microvesicles will preferably contain radioactive gases such as $Xe^{133}$ or $Kr^{81}$ or mixtures thereof, optionally in admixture with air, $CO_2$, oxygen, nitrogen, helium, kripton or any of the halogenated hydrocarbons as defined above.

The microvesicles according to the invention can be prepared according to any known method in the art. Typically, the manufacturing method involves the preparation of a precursor in the form of a dried powdered material comprising an amphiphilic material as above indicated, preferably by lyophilization (freeze drying) of an aqueous or organic suspension comprising said material.

For instance, as described in WO 91/15244, film-forming amphiphilic compounds can be first converted into a lamellar form by any liposome forming method. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustical or ultrasonic frequencies, and then freeze dried to form a free flowable powder which is then stored in the presence of a gas. Optional washing steps, as disclosed for instance in U.S. Pat. No. 5,597,549, can be performed before freeze drying.

According to an alternative embodiment (described for instance in U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed in International patent application WO2004/069284, a phospholipid (selected among those cited above and including at least one of the above-identified charged phospholipids) and a lyoprotecting agent (such as those previously listed, in particular carbohydrates, sugar alcohols, polyglycols and mixtures thereof) can be dispersed in an emulsion of water with a water immiscible organic solvent (e.g. branched or linear alkanes, alkenes, cycloalkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art, such as, for instance, sonication, shaking, high pressure homogenization, micromixing, membrane emulsification, high speed stirring or high shear mixing. For instance, a rotor-stator homogenizer can be employed, such as Polytron® PT3000. The agitation speed of the rotor-stator homogenizer can be selected depending from the components of the emulsion, the volume of the emulsion, the relative volume of organic solvent, the diameter of the vessel containing the emulsion and the desired final diameter of the microdroplets of solvent in the emulsion. Alternatively, a micromixing technique can be employed for emulsifying the mixture, e.g. by introducing the organic solvent into the mixer through a first inlet (at a flow rate of e.g. 0.05-5 ml/min), and the aqueous phase a second inlet (e.g. at a flow rate of 2-100 ml/min). The outlet of the micromixer is then connected to the vessel containing the aqueous phase, so that the aqueous phase drawn from said vessel at subsequent instants and introduced into the micromixer contains increasing amounts of emulsified solvent. When the whole volume of solvent has been added, the emulsion from the container can be kept under recirculation through the micromixer for a further predetermined period of time, e.g. 5-120 minutes, to allow completion of the emulsion. Depending on the emulsion technique, the organic solvent can be introduced gradually during the emulsification step or at once before starting the emulsification step. Alternatively the aqueous medium can be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microvesicles suspension where the dimensions and size distribution of the microvesicles are substantially comparable with the dimensions and size distribution of the suspension of microdroplets.

A further process for preparing gas-filled microvesicles comprises generating a gas microvesicle dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product. An example of this process is given, for instance, in WO97/29782, here enclosed by reference.

Spray drying techniques (as disclosed for instance in U.S. Pat. No. 5,605,673) can also be used to obtain a dried powder, reconstitutable upon contact with physiological aqueous carrier to obtain gas-filled microvesicles.

The dried or lyophilised product obtained with any of the above techniques will generally be in the form of a powder or a cake, and can be stored (e.g. in a vial) in contact with the desired gas. The product is readily reconstitutable in a suitable physiologically acceptable aqueous liquid carrier (typically injectable) in the presence of any of the above mentioned gases, to form the gas-filled microvesicles upon gentle agitation of the suspension.

Microvesicles according to the invention may optionally comprise a targeting ligand, a diagnostic agent and/or a bioactive agent, either included into the microvesicle structure or associated therewith.

The term "targeting ligand" includes within its meaning any compound, moiety or residue having, or being capable to promote, a targeting activity (e.g. including a selective binding) of the microvesicles of a composition of the invention towards any biological or pathological site within a living body. Targets with which targeting ligand may be associated include tissues such as, for instance, myocardial tissue (including myocardial cells and cardiomyocites), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

Examples of suitable targets and targeting ligands are disclosed, for instance, in U.S. Pat. No. 6,139,819, which is herein incorporated by reference.

The targeting ligand can be a compound per se which is admixed with the other components of the microvesicle or can be a compound which is bound to an amphiphilic molecule employed for the formation of the microvesicle.

In one preferred embodiment, the targeting ligand can be bound to an amphiphilic molecule of the microvesicle through a covalent bond. In such a case, the specific reactive moiety that needs to be present on the amphiphilic molecule will depend on the particular targeting ligand to be coupled thereto. As an example, if the targeting ligand can be linked to the amphiphilic molecule through an amino group, suitable reactive moieties for the amphiphilic molecule may be isothiocyanate groups (that will form a thiourea bond), reactive esters (to form an amide bond), aldehyde groups (for the formation of an imine bond to be reduced to an alkylamine bond), etc.; if the targeting ligand can be linked to the amphiphilic molecule through a thiol group, suitable complementary reactive moieties for the amphiphilic molecule include haloacetyl derivatives or maleimides (to form a thioether bond); and if the targeting ligand can be linked to the amphiphilic molecule through a carboxylic group, suitable reactive moieties for the amphiphilic molecule might be amines and hydrazides (to form amide or alkylamide bonds). In order to covalently bind a desired targeting ligand, at least part of the amphiphilic compound forming the microvesicle shall thus contain a suitable reactive moiety and the targeting ligand containing the complementary functionality will be linked thereto according to known techniques, e.g. by adding it to a dispersion comprising the amphiphilic components of the microvesicle. Preferably, the amphiphilic compound is a lipid bearing a hydrophilic polymer, such as those previously mentioned, preferably a pegylated phospholipid. In this case, the targeting ligand is linked to a suitable reactive moiety on the hydrophilic polymer. The amphiphilic compound can be combined with the desired targeting ligand before preparing the microvesicle, and the so obtained combination can be used in the preparation process of the microvesicle. Alternatively, the targeting ligand can be linked to the respective amphiphilic compound during the preparation process of the microvesicle.

According to an alternative embodiment, the targeting ligand may also be suitably associated with the microvesicle via physical and/or electrostatic interaction. As an example, a functional moiety having a high affinity and selectivity for a complementary moiety can be introduced into the amphiphilic molecule, while the complementary moiety will be linked to the targeting ligand. For instance, an avidin (or streptavidin) moiety (having high affinity for biotin) can be covalently linked to a phospholipid (or to a pegylated phospholipid) while the complementary biotin moiety can be incorporated into a suitable targeting ligand, e.g. a peptide or an antibody. The biotin-labelled targeting ligand will thus be associated with the avidin-labelled phospholipid of the microvesicle by means of the avidin-biotin coupling system. Alternatively, both the phospholipid and the targeting ligand can be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate with or bind to the targeting ligand to the amphiphilic molecules.

According to an alternative embodiment, the targeting ligand can be a compound which is admixed with the components forming the microvesicle, to be eventually incorporated the microvesicle structure, such as, for instance, a lipopeptide as disclosed e.g. in International patent Applications WO 98/18501 or 99/55383, both herein incorporated by reference.

Alternatively, a microvesicle can first be manufactured, which comprises a compound (lipid or polymer-modified lipid) having a suitable moiety capable of interacting with a corresponding complementary moiety of a targeting ligand; thereafter, the desired targeting ligand is added to the microvesicle suspension, to bind to the corresponding complementary moiety on the microvesicle. Examples of suitable specific targets to which the microvesicles can be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference.

The term "diagnostic agent" includes within its meaning any compound, composition or particle which may be used in connection with methods for imaging an internal region of a patient and/or diagnosing the presence or absence of a disease in a patient. In particular, diagnostic agents incorporated into or associated with a microvesicle in a composition of the invention are any compound, composition or particle which may allow imaging enhancement in connection with diagnostic techniques, including, magnetic resonance imaging, X-ray, in particular computed tomography, optical imaging, nuclear imaging or molecular imaging. Examples of suitable diagnostic agents are, for instance, magnetite nanoparticles, iodinated compounds, such as Iomeprol®, or paramagnetic ion complexes, such as hydrophobic gadolinium complexes.

The term "therapeutic agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including diagnosis, prevention, alleviation, pain relief or cure) of any pathological status in a patient (including malady, affliction, disease lesion or injury). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmides. Among these, drugs or pharmaceuticals are preferred.

The microvesicles of the invention can also be associated with other components such as, for instance, liposomes or micelles, Said components can simply be admixed together with the microvesicles or can form an assembly through a physical and/or chemical interaction with the stabilizing envelope of the microvesicles, e.g through a covalent bound, an electrostatic or ionic interaction, Van der Waals interaction, hydrophobic or hydrophylic interaction. Examples of these associated microvesicles compositions and of the preparation thereof are disclosed, for instance, in U.S. Pat. No. 6,258,378 and in International Patent Applications WO2005/063305 and WO2005/063306, all herein incorporated by reference. These components associable or associated with the microvesicles can in turn bear any of the above listed targeting ligands, diagnostic agents of bioactive agents, which will thus be associated with the microvesicles through said associated component. For instance, magnetite nanoparticles can be admixed with a charged amphiphilic material, such as those previously mentioned, in order to stabilize said particles and keep them dispersed in an aqueous solution (as disclosed for instance in U.S. Pat. No. 5,545,395, herein incorporated by reference), in order to associate it with a microvesicle. Alternatively, gadolinium complexes can be admixed with suitable micelle-forming compounds, for instance as disclosed in European Patent EP 804 251 (herein incorporated by reference), and the formed micelle can be associated with a microvesicle. Similarly, a therapeutic agent can be prepared as a micellar or liposomal suspension and as such being associated with a microvesicle.

The microvesicles according to the invention are preferably stored in dried powdered form and as such can advantageously be packaged in a two component diagnostic and/or therapeutic kit, preferably for administration by injection. The kit preferably comprises a first container, containing the lyophilized composition in contact with a selected microvesicle-forming gas and a second container, containing a physiologically acceptable aqueous carrier. Examples of suitable carriers are water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like). Said two component kit can include two separate containers or a dual-chamber container. In the former case the container is preferably a conventional septum-sealed vial, wherein the vial containing the lyophilized residue is sealed with a septum through which the carrier liquid may be injected using an optionally prefilled syringe. In such a case the syringe used as the container of the second component is also used then for injecting the contrast agent. In the latter case, the dual-chamber container is preferably a dual-chamber syringe and once the lyophilisate has been reconstituted and then suitably mixed or gently shaken, the container can be used directly for injecting the contrast agent.

The microvesicles of the present invention can be used in a variety of diagnostic and/or therapeutic techniques, including in particular ultrasound and Magnetic Resonance. The term diagnostic imaging includes within its meanings any method where the use of the contrast agent allows enhancing the visualisation of a portion or of a part of an animal (including humans) body, including imaging for preclinical and clinical research purposes. The term therapeutic imaging includes within its meaning any method for the treatment of a disease in a patient which comprises the use of a contrast agent (e.g. for the delivery of a bioactive compound to a selected targeted site or tissue) and which is capable of exerting or responsible to exert a biological effect in vitro and/or in vivo. Possible other diagnostic imaging applications include scintigraphy, light imaging, and X-ray imaging, including X-ray phase contrast imaging. A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used. Microvesicles according to the invention can typically be administered in a concentration of from about 0.01 to about 1.0 µl of gas per kg of patient, depending e.g. from their respective composition, the tissue or organ to be imaged and/or the chosen imaging technique. This general concentration range can of course vary depending from specific imaging applications, e.g. when signals can be observed at very low doses such as in colour Doppler or power pulse inversion.

The following examples will help to further illustrate the invention.

EXAMPLES

In the following examples, the number of gas-filled microvesicles in the suspensions and the volume of gas contained therein is determined by means of a Coulter counter (Counter Mark II apparatus fitted with a 30 µm aperture with a measuring range of 0.7 to 20 µm).

Example 1

A suspension is prepared by dissolving 120 mg of DAPC and 70 mg of DPPS in 100 ml of an aqueous suspension comprising 4 g of glycerol and 1 g of polypropylene glycol. The mixture is heated at 70° C. and then extruded 3 times through 0.2 µm polycarbonate membranes (Nuclepore®). The resulting suspension is then homogenized under high speed mechanical agitation using Megatron® (20'000 rpm and 3 min.) under $C_4F_{10}$ gas. The resulting suspension is centrifuged to remove excess lipid particles, glycerol and propylene glycol, re-suspended in 10% dextran (MW 15000) and distributed in 10 ml glass vials. The vials (each containing 2 ml of suspension) are frozen at −45° C. and lyophilized under a reduced pressure of 20 mbar. The obtained dried sample are exposed to $C_4F_{10}$ in a vial and then reconstituted with 2 ml of sterile water.

The concentration of microvesicles in the suspension, measured as above described, was of about $4.26 \cdot 10^9$ microvesicles/ml. This amount is normalized at 100% in the results of table 1, where this preparation is identified as preparation 1A.

The above preparation is repeated, but adding about 0.50% by moles (3.2 mg), 10% by moles (6.6 mg), 2% by moles (13 mg), 3% by moles (20 mg) and 5% by moles (34 mg) of DPPE-PEG2000 to the initial mixture, respectively, thus obtaining corresponding preparations 1B, 1C, 1D, 1E and 1F. Table 1 shows the normalized amount of microvesicles measured for this further four preparations.

TABLE 1

Amount of polymer-modified lipid vs. conc. of microvesicles

| Preparation | Concentration of DPPE-PEG2000 (mol. %) | Number of microvesicles (%) |
|---|---|---|
| 1A | — | 100 |
| 1B | 0.5 | 100 |
| 1C | 1 | 100 |
| 1D | 2 | 60 |
| 1E | 3 | 40 |
| 1F | 5 | 30 |

As inferable from the above table, excessive amounts of polymer-modified lipids may negatively affect the amount of obtained microvesicles.

Example 2

60 mg of DAPC, 30 mg of DPPG-Na and 4 g of PEG4000 are dispersed in 20 ml of tert-butanol at 60° C., until obtaining a clear solution. The solution is then placed in a round glass bottle, then frozen at −45° C. and lyophilized under a reduced pressure of 20 mbar. The obtained dried sample is placed in 20 ml glass vials and exposed to $SF_6$ (100 mg of lyophilized/vial) and then reconstituted with 10 ml of saline (0.9% NaCl).

The concentration of microvesicles in the suspension, measured as above described, was of about $1.90 \cdot 10^9$ microvesicles/ml. This amount is normalized at 100% in the results of table 2, where this preparation is identified as preparation 2A.

The above preparation is repeated, but adding about 0.46% by moles (1.5 mg), 0.97% by moles (3.2 mg), 1.51% by moles (5 mg), 2.97% by moles (10 mg) and 7.12% by moles (40 mg) of DPPE-PEG2000 to the initial mixture, respectively, thus obtaining corresponding preparations 2B, 2C, 2D, 2E and 2F. Table 2 shows the normalized amount of microvesicles measured for this further four preparations.

TABLE 2

Amount of polymer-modified lipid vs. conc. of microvesicles

| Preparation | Concentration of DPPE-PEG2000 (mol. %) | Number of microvesicles (%) |
|---|---|---|
| 2A | — | 84 |
| 2B | 0.46 | 100 |
| 2C | 0.97 | 93 |
| 2D | 1.51 | 62 |
| 2E | 2.97 | 53 |
| 2F | 7.12 | 39 |

As inferable from the above table, excessive amounts of polymer-modified lipids may negatively affect the amount of obtained microvesicles.

Example 3

Various suspension of gas-filled microvesicles (identified as preparations 3A to 2F in table 2) are prepared according to the following method: 25 mg of a mixture of DSPC/DSPA (in different molar ratios, as indicated in table 3) are dissolved in 4 ml of cyclooctane with an ultrasound probe until complete dissolution. This organic phase is added to 50 ml of a PEG4000 10% solution homogenized under high speed mechanical agitation using Megatron® (11,000 rpm and 3 min.) The resulting emulsion is heated for one hour at 80° C. under agitation and distributed in 10 ml glass vials. The vials (each containing 1 ml of suspension) are frozen at −50° C. and lyophilized under a reduced pressure of 0.2 mbar. The obtained dried sample are exposed to 35/65 (vol./vol.) mixture of $C_4F_{10}/N_2$ in a vial and then reconstituted with 2 ml of sterile water.

The same preparations as above are repeated, but adding 0.5% by moles or 1% by moles of DSPE-PEG to the mixture (see table 3, to obtain corresponding preparations 3A' to 3F'.

The concentration of microvesicles has then been measured on each of the above preparation, right after the preparation and after 6 hours. Table 3 shows the results, indicating the percentage of microvesicles left after the 6 hours stay for each preparation.

TABLE 3

Influence of polymer-bearing lipids on microvesicles' stability

| Preparation | DSPC/DSPA ratio | Type and amount of pegylated lipid (in % by moles) | Amount of microvesicles after 6 hours (in % with respect to initial amount) |
|---|---|---|---|
| 3A | 90/10 | — | 64% |
| 3A' | 90/10 | DSPE-PEG5000 0.5% | 84% |
| 3B | 80/20 | — | 57% |
| 3B' | 80/20 | DSPE-PEG5000 0.5% | 90% |
| 3C | 70/30 | — | 67% |
| 3C' | 70/30 | DSPE-PEG5000 0.5% | 96% |
| 3D | 90/10 | — | 46% |
| 3D' | 90/10 | DSPE-PEG2000 1.0% | 83% |
| 3E | 80/20 | — | 48% |
| 3E' | 80/20 | DSPE-PEG2000 1.0% | 83% |
| 3F | 95/5 | — | 45% |
| 3F' | 95/5 | DSPE-PEG2000 1.0% | 85% |

The above results show that minimal amounts of polymer-modified lipids allows to preserve relatively high amounts of microvesicles after 6 hour, differently from the preparations where no polymer-modified lipid is present.

Example 4

Six gas-filled microvesicles composition (4A to 4F in table 4) with different amounts on DPPE-MPEG5000 (see table 4) are prepared as follows.

25 mg of a mixture of DSPC/DSPA (80/20 molar ratio) are dissolved in 4 ml of cyclooctane with an ultrasound probe until complete dissolution. This organic phase is added to 50 ml of a PEG4000 10% solution homogenized under high speed mechanical agitation using Megatron® (11,000 rpm and 3 min.) The emulsion is heated for one hour at 80° C. under agitation then diluted in one volume of PEG4000 10% solution. The resulting emulsion is distributed in 10 ml glass vials. The vials (each containing 0.75 ml of suspension) are frozen at −50° C. and lyophilized under a reduced pressure of 0.2 mbar. The obtained dried sample are exposed to $C_4F_{10}/N_2$ 35/65 mixture in a vial and then reconstituted with 1.5 ml of saline solution.

The amount of gas entrapped in the obtained microvesicles and the total number of microvesicles in each of the above preparations is then measured by Coulter® measurement, The following table 4 shows the measures of gas volume.

TABLE 4

Amount of gas entrapped into microvesicles

| Preparation no. | PE-PEG molar conc. (in %) | μl of gas per ml of suspension in microvesicles with diameter | |
|---|---|---|---|
| | | ≤8 μm | 2-8 μm |
| 4A | — | 3.4 | 3.1 |
| 4B | 0.15 | 5.1 | 4.5 |
| 4C | 0.5 | 6.2 | 5.3 |
| 4D | 1.0 | 6.0 | 5.0 |
| 4E | 3.0 | 4.9 | 3.9 |
| 4F | 6.0 | 4.6 | 3.4 |

As inferable from the above results, low amounts of polymer-modified lipids in the composition of the stabilized microvesicles allow incorporating relatively high amounts of gas in the microvesicles.

The amount of microvesicles in the suspension after 6 hours has then been measured and compared with the amount in the respective initial suspensions. The results are given in the following table 5.

TABLE 5

Stability of microvesicles at different concentrations of polymer-bearing lipid after 6 hours

| Preparation no. | PE-PEG molar conc. (in %) | Amount of microvesicles after 6 hours (in % with respect to initial amount) | |
|---|---|---|---|
| | | Diameter ≤8 μm | Diameter ≤2 μm |
| 4A | — | 55% | 28% |
| 4B | 0.15 | 61% | 43% |
| 4C | 0.5 | 85% | 82% |
| 4D | 1.0 | 96% | 97% |
| 4E | 3.0 | 100% | 100% |
| 4F | 6.0 | 84% | 84% |

The invention claimed is:

1. Aqueous suspension of gas-filled microvesicles, wherein said microvesicles have a stabilizing envelope comprising a first phospholipid and from 0.15% by mole to 1% by mole of a polymer-modified lipid consisting of a lipid covalently bound to a hydrophilic polymer, wherein said lipid is a second phospholipid and said hydrophilic polymer is polyethyleneglycol.

2. A suspension according to claim 1 comprising at least 0.3% by mole of said lipid covalently bound to a hydrophilic polymer.

3. A suspension according to claim 1 comprising about 0.5% by mole of said lipid covalently bound to a hydrophilic polymer.

4. A suspension according to claim 1, wherein said second phospholipid is a phosphatidylethanolamine.

5. A suspension according to claim 4 wherein said phosphatidylethanolamine is a fatty acid di-ester of phosphatidylethanolamine.

6. A suspension according to claim 1 wherein said polyethyleneglycol has a molecular weight of from about 500 to about 50,000 Daltons.

7. A suspension according to claim 1 wherein said polyethyleneglycol has a molecular weight of from about 1,000 to about 20,000 daltons.

8. Aqueous suspension of gas-filled microvesicles, wherein said microvesicles have a stabilizing envelope comprising a first phospholipid and from 0.15% by mole to 1% by mole of a polymer-modified lipid comprising a lipid covalently bound to a hydrophilic polymer, wherein said polymer-modified lipid contains no targeting ligand, and wherein said lipid is a second phospholipid and said hydrophilic polymer is polyethyleneglycol.

9. A suspension according to claim 8 comprising at least 0.3% by mole of said lipid covalently bound to a hydrophilic polymer.

10. A suspension according to claim 8 comprising about 0.5% by mole of said lipid covalently bound to a hydrophilic polymer.

11. A suspension according to claim 8, wherein said second phospholipid is a phosphatidylethanolamine.

12. A suspension according to claim 11 wherein said phosphatidylethanolamine is a fatty acid di-ester of phosphatidylethanolamine.

13. A suspension according to claim 8 wherein said polyethyleneglycol has a molecular weight of from about 500 to about 50,000 Daltons.

14. A suspension according to claim 8 wherein said polyethyleneglycol has a molecular weight of from about 1,000 to about 20,000 daltons.

* * * * *